United States Patent [19]

Otten et al.

[11] Patent Number: 5,187,191

[45] Date of Patent: Feb. 16, 1993

[54] LIQUID ANALOGS OF CERTAIN POLYOXYALKYLENE COMPOUNDS HAVING A PLURALITY OF HETERIC POLYOXYPROPYLENE/POLYOXYETHYLENE CHAINS AS DISPERSANTS FOR PESTICIDAL FORMULATIONS

[75] Inventors: Jay G. Otten, Flat Rock, Mich.; Kenneth F. Schoene, West Milford, N.J.

[73] Assignee: BASF Corp., Parsippany, N.J.

[21] Appl. No.: 675,785

[22] Filed: Mar. 27, 1991

Related U.S. Application Data

[63] Continuation-in-part of Ser. No. 494,028, Mar. 5, 1990, abandoned.

[51] Int. Cl.$^5$ .................... A01N 25/02; A61K 47/00
[52] U.S. Cl. ................... 514/772.3; 424/400
[58] Field of Search ............... 424/78, 400; 514/772.3

[56] References Cited

U.S. PATENT DOCUMENTS

| | | | |
|---|---|---|---|
| 2,674,619 | 4/1954 | Lundsted | 560/186 |
| 3,022,335 | 2/1962 | Lundsted | 528/419 |
| 3,101,374 | 8/1963 | Patton, Jr. | 544/398 |
| 3,639,575 | 2/1972 | Schmolka | 424/78 |
| 4,474,912 | 10/1984 | Ozmeral et al. | 514/941 |
| 4,780,245 | 10/1989 | Burke et al. | 252/312 |
| 4,810,503 | 3/1989 | Carson et al. | 424/78 |
| 4,851,421 | 7/1989 | Iwasaki et al. | 424/405 |

Primary Examiner—Thurman K. Page
Assistant Examiner—Peter F. Kulkosky

[57] ABSTRACT

A stable, aqueous pesticide dispersion composition comprising:
(a) a water insoluble pesticide;
(b) a polyoxyalkylene copolymer having surface active properties, said copolymer having the formula

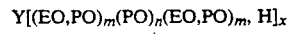

$$Y[(EO,PO)_m(PO)_n(EO,PO)_{m'}H]_x$$

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EO,PO) represents a hydrophilic heteric block having an oxygen/carbon ratio of more than 0.40, m, m' and n are numbers such that the total molecular weight of said hydrophilic heteric block is from about 660 to 4,400, the total molecular weight of said PO hydrophobe is from about 1600 to 3600 and the total molecular weight of said copolymer ranges from about 2200 to 8000, said copolymer being about 30 to 55 weight percent hydrophilic with said hydrophilic heteric block comprising from about 5 to 40 weight percent of PO; and
(c) water.

6 Claims, No Drawings

LIQUID ANALOGS OF CERTAIN POLYOXYALKYLENE COMPOUNDS HAVING A PLURALITY OF HETERIC POLYOXYPROPYLENE/POLYOXYETHYLENE CHAINS AS DISPERSANTS FOR PESTICIDAL FORMULATIONS

This is a continuation-in-part of copending application(s) Ser. No. 07/494,028 filed on Mar. 5, 1990, now abandoned.

BACKGROUND OF THE INVENTION

1. Field of the Invention

The present invention relates to the use of analogs of certain liquid polyoxyethylene compounds having a plurality of heteric polyoxypropylene-polyoxyethylene chains as dispersants for pesticidal compositions.

2 Description of the Related Art

Patton, U.S. Pat. No. 3,101,374 discloses a method for making surface-active agents which have a conjugated or blocked polymer structure employing a hydrophobic oxyalkylene, usually oxyporpylene, chain or chains as a nucleus and being characterized by having a heteric oxyethylene chain or chains attached to the hydrophobic oxyalkylene chain. Patton discloses that heteric hydrophilic oxyethylene chains may be composed of oxyethylene groups having defined proportions of different and higher molecular weight oxyalkylene groups, such as oxypropylene or oxybutylene groups, randomly distributed throughout the hydrophilic oxyethylene chain. Patton states that by adding a certain percentage of propylene oxide or other higher molecular weight alkylene oxide to the ethylene oxide that is condensed with the hydrophobic polyoxyalkylene polymer, it is possible to produce liquid products which are sparkling clear, mobile liquids. These liquids are more fluid and have appreciably lower viscosities than do compositions prepared by the addition of 100 percent ethylene oxide to the same hydrophobic polyoxyalkylene polymer.

Lundsted, U.S. Pat. No. 3,022,335, discloses the reverse structures of Patton. Specifically, Lundsted relates to surface activity polyoxyalkylene compounds having a plurality of heteric polyoxypropylene-polyoxyethylene chains.

SUMMARY OF THE INVENTION

The present invention relates to the use of analogs of certain liquid polyoxyalkylene compounds having a plurality of heteric polyoxypropylene polyoxyethylene chains as dispersants for pesticidal formulations.

In the dispersant of the present invention, 5 to 40 weight percent of ethylene oxide in the hydrophile is replaced by propylene oxide to make the liquid dispersant. The pesticidal compositions so formed do not require as much agitation to bring a powdered pesticide into a useable, homogeneous aqueous suspension.

DETAILED DESCRIPTION OF THE PREFERRED EMBODIMENT

The present invention relates to the use of the liquid analogues of certain polyoxyalkylene compounds, these analogues having a plurality of heteric polyoxyalkylene chains as dispersants for pesticidal formulations. The polyoxyalkylene compounds are formed as disclosed in the U.S. Pat. No. 3,101,374 incorporated herein by reference, and are the analogues of polyoxyethylene-polyoxypropylene block copolymers having about a 1600 to 3600 molecular weight of the hydrophobe and are 30 to 55 weight percent hydrophile, the hydrophile having a molecular weight from about 660 to 4400, and the dispersant copolymer having a total molecular weight of from about 2200 to 8000. These surfactants have the formula $$Y[(EO,PO)_m(PO)_n(EO,PO)_{m'}H]_x$$

wherein Y is the nucleus of an organic reactive hydrogen compound containing x reactive hydrogen atoms and having up to 6, inclusive, carbon atoms, x is an integer, and m, m' and n are numbers such that the total molecular weight of the hydrophobe, hydrophile and the dispersant are as set forth above. These surfactants are usually pastes at room temperature and are made lower melting or liquid by the substitution of propylene oxide for 5 to 40% of the ethylene oxide present in the hydrophilic polyoxyethylene blocks. Thus, the surfactant comprises heteric hydrophilic block portions and block hydrophobic portions. The resulting liquid dispersants offer ease of handling and eliminate the problem of airborne particulates attendant with the mixing of powdered pesticides with water and powdered or non-heteric block dispersants. By use of the present invention, the pesticide is already dispersed in the liquid dispersant. The user need only pour the pesticide dispersant mixture into water to form an aqueous dispersion of pesticide.

The hydrophobic element of the liquid dispersant is a polyoxyalkylene polymer in which at least most of the individual oxyalkylene groups contained therein have at least 3 carbon atoms in their structure. An essential characteristic of the hydrophobic element of the compounds is that the total hydrophobic alkylene oxide ingredient therein has an average oxygen/carbon atom ratio of not greater than 0.40. Since oxypropylene groups have an oxygen/carbon atom ratio of 0.33, the oxyalkylene ingredient used in making the hydrophobic portion of the compositions can be propylene oxide or mixtures thereof with ethylene oxide or butylene oxide or other higher molecular weight alkylene oxides with the proportions used being such that the oxygen/carbon atom ratio does not exceed 0.40.

The hydrophilic elements of these compounds are polymeric chains of oxyethylene groups having higher molecular weight oxyalkylene groups which contain at least 3 carbon atoms in their structure randomly and intermittently distributed therein. Since the oxypropylene group is the group most frequently incorporated in the hydrophilic chain with the oxyethylene groups, henceforth, for the sake of convenience in description, such hydrophilic chains are referred to, at times, simply as heteric polyoxyethylene-polyoxypropylene chains. It will be recognized, however, that wherever this term is used other higher oxyalkylene groups such as the oxybutylene group, the oxyamylene and the oxystyrene group, may be used in lieu of the oxypropylene group.

These conjugated polyoxyalkylene compounds are prepared by first condensing the hydrophobic alkylene oxide ingredients, described above, having an average oxygen/carbon atom ratio of not greater than 0.40 with an organic reactive hydrogen compound containing one or a plurality of reactive hydrogen atoms and having up to about 6 carbon atoms to prepare a hydrophobic polyoxyalkylene intermediate having a molecular weight of at least about 1600, and subsequently condensing therewith a mixture of ethylene oxide and a higher molecular weight alkylene oxide. The mixture of ethylene oxide and higher molecular weight alkylene oxide employed should contain at least about 5 weight percent of the higher molecular weight alkylene oxide but must have an average oxygen/carbon atom ratio of greater than 0.40. The conjugated polyoxyalkylene compounds of this invention conform to the following generic formula:

$$Y[(E,P)_m(P)_n(E,P)_m H]_x \qquad (I)$$

wherein Y is the nucleus of an organic reactive hydrogen compound containing x reactive hydrogen atoms and having up to 6, inclusive, carbon atoms, x is an integer, (P) is a hydrophobic polyoxyalkylene chain having an oxygen/carbon atom of not more than 0.40, the molecular weight of P and the value of x being such that the molecular weight of (P) is at least about 1600 and up to about 3600, and E is a hydrophilic heteric polyoxyalkylene chain which (1) contains oxyethylene groups and at least 5%, by weight, of higher molecular weight oxyalkylene groups having at least 3 carbon atoms in their structure and (2) has an average oxygen/carbon atom ratio of greater than 0.40, E being present in the composition to the extent that it constitutes from about 18-52 weight percent of the total molecule.

The hydrophobic polyoxyalkylene polymer, which is an intermediate in the preparation in the compounds of this invention, has the following structure:

$$Y(-P-H)_x \qquad (II)$$

wherein Y, P, and x are defined as in Formula I above and the molecular weight of the hydrophobic polyoxyalkylene polymer is at least about 1600 and may range up to 3600 or higher. The most preferred range is about 2000–3500.

When P in Formula II above is a polymeric chain of oxypropylene groups, the hydrophobic polyoxyalkylene polymer is a polyoxypropylene polymer having the formula:

$$Y[(C_3H_6O)_n - H]_x \qquad (III)$$

wherein Y and x are defined as in Formula I above, and n is an integer. In an illustrative example, when Y is the nucleus of propylene glycol and P is a polymeric chain of oxypropylene groups, the hydrophobic polyoxypropylene polymer is simply a polyoxypropylene glycol. When Y is the residue of n-propanol, the polyoxypropylene polymer is simply the n-propyl ether of a polyoxypropylene glycol. When Y is the residue of a dibasic organic acid, such as adipic acid, the polyoxypropylene polymer has the following structure:

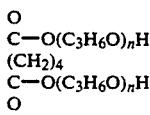

When P of Formula II is a polymeric chain of oxybutylene groups, the hydrophobic polyoxyalkylene polymer has the following structure:

$$Y[(C_4H_8O)_n - H]_x \qquad (IV)$$

wherein Y, n and x are defined as previously set forth.

The molecular weight required in the hydrophobic polyoxyalkylene polymer to obtain surface active or dispersive properties depends upon both the number of carbon atoms in the alkylene oxide or oxides used in making the hydrophobic polyoxyalkylene intermediate and the reactive hydrogen compound used in initiating the polymerization of the hydrophobic alkylene oxide ingredient. When the hydrophobic polyoxyalkylene intermediate is prepared by condensing propylene oxide with a reactive hydrogen compound containing two reactive hydrogen atoms, a minimum molecular weight of about 1 600 is required. When the hydrophobic polyoxyalkylene intermediate is prepared by condensing butylene oxide with a reactive hydrogen compound containing a plurality of reactive hydrogen atoms, a molecular weight of about less than 1600 may be required.

The compounds of this invention are prepared by condensing a mixture of ethylene oxide and a higher molecular weight alkylene oxide having at least 3 carbon atoms in its structure with the hydrophobic polyoxyalkylene intermediate in an amount such that the higher molecular weight alkylene oxide constitutes 5–40%, by weight, of the resultant hydrophile. The mixture of ethylene oxide and higher molecular weight alkylene oxide employed in the hydrophilic portion of the compounds of this invention must contain at least 5%, by weight, of the higher molecular weight alkylene oxide and have an average oxygen/carbon atom ratio of greater than 0.40. Preferably, at least 10% of the higher molecular weight alkylene oxide is used.

In preparing the hydrophobic polyoxyalkylene intermediate, the condensation of propylene oxide, for example, with the reactive hydrogen compound is normally carried out at elevated temperatures and pressures in the presence of an alkaline catalyst such as a sodium alkoxide, a quaternary ammonium base, sodium hydroxide or preferably potassium hydroxide. Similarly, the condensation reaction may be carried out in the presence of acid catalysts as set forth in U.S. Pat. No. 2,510,540.

Although the reaction may be carried out by simply heating a mixture of the reactants under pressure at a sufficiently high temperature, this procedure is not ordinarily used as the temperatures and pressures required are excessive and control of the reaction is difficult. For each mole of propylene oxide reacting, as estimated 25 kilogram-calories of heat is liberated which, in the presence of a large quantity of propylene oxide, may increase the temperature and reaction rate to such an extent that the reaction assumes explosive nature.

The preferred method of carrying out the preparation of the hydrophobic intermediate is to add the propylene oxide to a stirred, heated mixture of the desired reactive hydrogen compound and alkaline catalyst in a sealed reaction vessel. By adding the propylene oxide to the reaction vessel at such a rate that it rapidly reacts, an excess of propylene oxide is avoided and control of the reaction is simplified.

The temperature at which the hydrophobic intermediate is prepared depends upon the particular system in question and especially upon the catalyst concentration used. Generally, at higher catalyst concentrations the reaction can be run at lower temperatures and correspondingly lower pressures. The temperatures and pressures required for any given reaction will vary with the reactive hydrogen compound and the type and concentration of catalyst used. The condensation of the mixture of ethylene oxide and propylene oxide or other higher molecular weight alkylene oxide is carried out in an analogous manner.

As noted heretofore, the hydrophobic polyoxyalkylene intermediate is prepared by condensing an alkylene oxide ingredient having an oxygen/carbon atom ratio of less than 0.40, such as propylene oxide, with a reactive hydrogen compound containing at least one, and preferably not more than about 6, reactive hydrogen atoms and having up to 6 carbon atoms. Since the reactive hydrogen compound constitutes only a small proportion of the total composition, it ordinarily does not have a significant influence on the properties thereof. In other words, the particular reactive hydrogen compound employed in preparing the conjugated polyoxyalkylene compounds is not critical so long as it furnishes at least one reactive hydrogen atom, and useful surface active compositions are obtained regardless of the particular reactive hydrogen compound employed in the preparation of the hydrophobic polyoxyalkylene polymer.

The term reactive hydrogen atom is well known and clearly understood by those skilled in the art. However, to remove any possible ambiguity in this regard, the term reactive hydrogen atom, as used herein and in the appended claims, includes any hydrogen atom fulfilling the following two conditions:

(1) It is sufficiently labile to open the epoxide ring of 1,2-propylene oxide or ethylene oxide, and (2) It reacts with methyl magnesium iodide to liberate methane in the classical Zerewitinoff reaction (see Niederl and Niederl, Micromethods of Quantitative Organic Analysis, p. 263, John Wiley and Sons, New York City, 1946).

The reactive hydrogen atoms which will fulfill the above two conditions are normally activated by being a member of a functional group containing an oxygen atom, e.g. a hydroxyl group, a phenol group, a carboxylic acid group; a basic nitrogen atom (e.g. an amine group, a hydrazine group, an imine group, an amide group, a guanidine group, a sulfonamide group, a urea group, a thiourea group; or a sulfur atom, e.g. a mercaptan, a thiophenol, a thiocarboxylic acid, hydrogen sulfide. Alternatively, certain hydrogen atoms may be activated by proximity to carbonyl groups such as those found in cyanoacetic esters, acetoacetic esters, malonic esters, as is well known in the art.

Thus, the lower molecular weight, monohydroxy alcohols constitute one class of reactive hydrogen compounds that is especially useful in preparing the compositions of this invention. Such alcohols can have up to about 6 inclusive, carbon atoms per molecule and examples of these materials are methanol, n-propanol, n-butanol, n-hexanol, methyl ether of ethylene glycol, and phenol.

In this connection, it probably would be well to point out that an alkoxide attached to a tertiary carbon atom has been recognized as being unreactive with alkylene oxides, such as ethylene oxide and propylene oxide, under conventional base-catalyzed reaction conditions, so such compounds as tertiary butanol, alpha-or beta-terpinol are not reactive hydrogen compounds adaptable for use in preparing the compositions of the invention. Actually, tertiary butanol has been recommended in the prior art as a solvent for base-eatalyzed alkylene oxide reactions because of its unreactivity therewith and we have found that alpha- and beta-terpinol do not react with ethylene oxide, or propylene oxide for that matter, under conventional basecatalysis conditions.

The lower molecular weight aliphatic polyhydric alcohols constitute another class of reactive hydrogen compounds that is especially useful in preparing the compositions of this invention. Such alcohols can have from about 2 to 6, inclusive, carbon atoms per molecule, and examples of these materials are ethylene glycol, propylene glycol, 2,3-butylene glycol, 1,3-butanediol, 1,5-pentanediol, 1,6-hexanediol, glycerol, trimethylolpropane, sorbitol, sucrose and the like. Another class of reactive hydrogen compounds that can be used is the alkylamines and alkylene polyamines having at least 2 reactive hydrogen atoms, such as methylamine, ethylamine, propylamine, butylamine, hexylamine, ethylenediamine, 1,6-hexanediamine, diethylenetriamine, and the like. Also, such cyclic amines as piperazine, 2-methylpiperazine and 2,5-dimethylpiperazine can also be used. Amides constitute a further class of such reactive hydrogen compounds, such as acetamide, succinamide and benzenesulfonamide. Yet another class of such reactive hydrogen compounds is the di- and polycarboxylic acids, such as adipic acid, succinic acid, glutaric acid, aconitic acid, diglycolic acid, and the like.

Other reactive hydrogen compounds that can be used are the secondary amines, such as dimethylamine, diethylamine, morpholine, N-ethylbutylamine, dipropylamine, N-methylethylamine, N-ethylpropylamine, and the like. A further class of reactive hydrogen compounds is N-monosubstituted amides, such as N-methylacetamide, N-ethylbenzenesulfonamide, N-propylethanesulfonamide, and the like. A still further class is monocarboxylic acids, such as acetic acid, benzoic acid, butanoic acid, and the like. Still other such reactive hydrogen compounds can also be used so long as the particular compound meets the requirements set forth, i.e., relatively low molecular weight, reactivity with ethylene oxide and only a single reactive hydrogen atom.

The amount of the hydrophobic alkylene oxide ingredient used has been expressed in terms of the molecular weight of the resulting reactive hydrogen compound-alkylene oxide condensate. It is to be understood that the term "molecular weight" means theoretical molecular weight throughout this specification and the claims. In expressing the molecular weight for the hydrophobic polyoxyalkylene intermediate, the molecular weight of the reactive hydrogen compound is included. This molecular weight should be, as stated earlier, at least about 1600 and can range up to about 3600 or higher. Compositions having the most desirable properties as detergents usually are based on a hydrophobic polyoxyalkylene intermediate having a molecular weight in the range of about 2000 to 3500.

The heteric polyoxyethylene chains constitute the hydrophilic element of the conjugated polyoxyalkylene compounds and must constitute a prescribed, although broad, proportion of the molecule. The hydrophilic polyoxyethylene content must be controlled to obtain a proper hydrophobic-hydrophilic balance, which is essential to obtain good surface active properties (e.g., dispersability).

The compounds herein described which contain 30 to 55%, by weight, of such heteric polyoxyethylene chains are in nearly all cases miscible with water in all proportions at room temperature. Optimum properties are usually obtained when the compounds contain 35 to 55% of heteric polyoxyethylene chains.

On the other hand, the compounds of this application which contain 5 to 20% of heteric polyoxyethylene chains which fall within the purview of the aforementioned '374 patent are only sparingly soluble in water at room temperature, but have a relatively high solubility in many nonpolar solvents. The principal applications of these compounds lie outside the field of dispersants. For example, because of their relatively high solubility in nonpolar solvents they may be employed as surface active agents in formulated dry cleaning solvents. Another outstanding characteristic of these compounds is their extraordinary ability to remove grease from raw wool, as measured by the method of Barnett and Powers (The Journal of the Society of Cosmetic Chemists, vol. II, page 219, 1951).

The heteric polyoxyethylene chains employed in the compositions of this invention contain about 8 to 95 oxyethylene groups and 1 to 30 oxypropylene groups or other higher molecular weight oxyalkylene groups, such as oxybutylene, oxystyrene or mixtures of such oxyalkylene groups. Where the heteric polyoxyethylene chains contain substantially less than about 5% of higher molecular weight oxyalkylene groups, the compositions do not differ materially from compositions in which the hydrophilic chains are straight polyoxyethylene chains. When 5-10% of oxypropylene groups, for example, are included in the heteric polyoxyethylene chains, the physical properties of the compositions are materially improved (as compared with compositions containing straight polyoxyethylene chains) in that they have lower viscosity and greater clarity than the compounds containing straight polyoxyethylene chains as the hydrophilic element. As the percent oxypropylene groups in the heteric polyoxyethylene chains is increased, the physical properties of the compositions such as viscosity, clarity and change in physical state from solid to paste to liquid show still further improvement, but the surface active properties are also noticeably modified. A practical upper limit on the amount of higher molecular weight alkylene oxide in the mixture with ethylene oxide used to produce the heteric polyoxyethylene chains is approximately 40%, for when this value is exceeded by any substantial amount the surface active properties of the compositions fall off rapidly.

It will be apparent from the foregoing discussion that the liquified surfactants used to make the compositions of this invention can be prepared using, specifically, a mixture of propylene oxide and ethylene oxide for condensation with an active hydrogen compound to form the hydrophobic polymer base and using a mixture of ethylene oxide and propylene oxide for condensation with the hydrophobic polymer base to form the hydrophilic chains, and thereby, a novel surface active compound. Furthermore, it has been disclosed that the relative percentages of propylene oxide and ethylene oxide employed in the first step to form the hydrophobic base can fall in the range of 60 to 100 weight percent propylene oxide and 40 to 0 weight percent ethylene oxide, while the relative percentages of propylene oxide and ethylene oxide employed in the mixture to form the hydrophilic chains can fall in the range of 95 to 40 weight percent ethylene oxide and 5 to 60 weight percent propylene oxide. It is thus apparent that, by choosing the extremes of these ranges, a product can be obtained which contains 60 weight percent propylene oxide and 40 weight percent ethylene oxide in both the hydrophobic base and the hydrophilic chains. Such a composition would not have surface activity and is not contemplated by the present invention. It will be noted that each of the appended claims in the '374 patent defines the compound of that invention as one having "surface active properties" and therefore the nonsurface active compound described above is not claimed therein. Furthermore, each of the claims specified in terms or equivalent language that the average oxygen to carbon atom ratio for the hydrophobic polymer base is not more than 0.40 and is greater than 0.40 for the hydrophilic chains condensed therewith. Thus, the eventuality discussed is literally avoided.

Fully equivalent products are expected when a higher molecular weight alkylene oxide other than propylene oxide is employed in the preparation of the heteric hydrophilic chains of the compounds. Examples of higher molecular weight alkylen oxides that may be employed include butylene oxide, amylene oxide, cyclohexene oxide, styrene oxide, etc. As in the case of propylene oxide, it is necessary to have at least 5%, by weight, of the higher molecular weight oxyalkylene units in the chain to obtain significant improvements in the properties of the compounds. Unlike propylene oxide, however, it is not feasible to incorporate 25% of the higher molecular weight oxyalkylene groups in the hydrophilic chains where the higher molecular weight oxyalkylene group contains 4 or more carbon atoms in its structure. Instead, the upper limit on the higher molecular weight oxyalkylene content must be reduced so that the hydrophilic chains have an average oxygen/carbon atom ratio of greater than 0.40.

As used herein, the term pesticide is intended to refer to toxicants and to biological compositions containing such chemicals which are effective in killing, preventing, or controlling the growth of undesirable pests, e.g. plants, insects, mites, microorganisms, algae, fungi, bacteria, and the like, said chemicals and compositions being commonly known as insecticides, mitocides, bactericides, algicides, fungicides, nematocides, herbicides, etc. Examples of specific known toxicants which may be employed in the composition of the invention are disclosed in U.S. Pat. No. 3,948,636, which disclosure is incorporated herein by reference.

More particularly the pesticides are selected from any of the known pesticides, particularly herbicides and insecticides. Particularly useful herbicides such as 2-chloro-2',6'-diethyl-N-(methoxymethyl)acetanilide; a, a, a-trifluoro-2,6-dinitro-N,N-dipropyl-p-toluidine and N-(1-ethylpropyl)-3,4-dimethyl-2,6-dinitrobenzenamine. Other useful biocides are listed in U.S. Pat. No. 3,317,305 incorporated herein by reference. Preferred pesticides include the following, identified first by the trademark, followed by the chemical name.

| | |
|---|---|
| Trifluralin | a, a, a-trifluoro-2,6-dinitro-N,N-dipropyl-p-toluidine |
| Atrazine | 2-chloro-4-ethylamino-6-isopropylamino-1,3,5-trazine |
| Alachlor | 2-chloro-2', 6'-diethyl-N-(methoxymethyl)acetanilide |
| Linuron | 3-(3,4-dichlorophenyl)-1-methoxy-1-methyl-urea |
| Diuron | 3-(3,4-dichlorophenyl)-1,1-dimethylurea |
| Methoxychlor | 2,2-bis(p-methoxyphenyl)-1,1,1-trichloroethane |
| Carbaryl | 1-naphthyl-N-methylcarbamate |

In the following section discussing the preparation of the nonionic surfactant dispersing agents, as well as in the examples, nonionic surfactant A is a polyoxyethylene polyoxypropylene block copolymer which is 45% by weight polyoxyethylene and has a total average molecular weight of about 4461 to 5204, and nonionic block surfactant B is a polyoxyethylene polyoxypropylene block copolymer which is 50% by weight polyoxyethylene and has a total average molecular weight of about 4795 to 5574.

The molecular weight was calculated from the typical hydroxyl numbers of the surfactants. A typical functionality of 1.67 was used for surfactant A and a typical functionality of 1.59 was used for surfactant B. The average functionality between surfactant A and B was 1.63. This was used to calculate the experimental molecular weight according to the following:

$$\frac{\text{functionality} \times 56{,}100}{\text{hydroxyl number}} = \text{molecular weight}$$

Preparation of the Nonionic Surfactant Dispersing Agents

The Surfactant A and Surfactant A+20 moles of propylene oxide (20 PO) surfactants were respectively prepared in two and three steps. The molecular weight increased with each step. Other nonionic Surfactant A analogs were prepared in a similar fashion.

| Nonionic Surfactant A 800 Molecular Weight Polypropylene Glycol Intermediates (P-800T) | |
| --- | --- |
| Propylene Glycol | 212 g |
| 90% KOH | 27 g |
| Propylene Oxide | 2477 g |

To the prepared one gallon autoclave, we charged the propylene glycol and 90% KOH. The reactor was sealed, purged, and the pressure was checked. The reactor was vented to 0 PSIG, heated to 125° C., and stirred for one hour. No further venting occurred, and at 125° C., we added PO at CA. 275 g/hr, 90 PSIG. When all reactants were added, we reacted the contents (at 125° C.) to constant pressure 2 hours min. The reactor was cooled to 100° C. and vented slowly. During venting, the volatiles were weighed. We evacuated the reactor to, 10 mmHg and stripped for one hour. We relieved the vacuum with nitrogen, cooled to 80° C., and discharged to a nitrogen flushed bottle. The hydroxyl number was 142 mg KOH/g.

| Nonionic Surfactant A | |
| --- | --- |
| P-800 T | 567 g |
| Propylene Oxide | 2406 g |
| Ethylene Oxide | 2430 g |

To a prepared two-gallon autoclave, we charged the P-800 T. The autoclave was sealed, purged, and the pressure was checked. While heating to 125° C., it was evacuated to, 10 mmHg, and stripped at 125° C. for thirty minutes. The vacuum was relieved with nitrogen to 0 PSIG. At 125° C., the PO was added at a rate of 330 g/hr<90 PSIG. When all reactants were added, they were reacted at (125° C.) to constant pressure for 3.5 hours minimum. The autoclave was vented slowly, and the volatiles weighed. The autoclave was heated to 145°–150° C. and pressurized with nitrogen gas to 34 PSIG. At 145°–150° C., EO was added at a rate of 800 g/hr<90 PSIG. When all reactants were added, we reacted EP to constant pressure, for 1.5 hr. minimum. The autoclave was cooled to 100° C. and vented slowly, and the volatiles weighed. The autoclave was evacuated carefully to <10 mmHg and stripped for one hour. The vacuum was relieved with nitrogen gas, and the contents discharged to nitrogen flushed bottles. The hydroxyl number was 19.9 mg KOH/g.

| Nonionic Surfactant A + 20 PO 400 Molecular Weight Polypropylene Glycol Intermediate (P-402T) | |
| --- | --- |
| Propylene Glycol | 705 g |
| 45% KOH | 107 g |
| Propylene Oxide | 4588 g |

To a prepared two gallon autoclave, we charged propylene glycol and KOH. The autoclave was sealed, purged and the pressure was checked at 50 PSIG. The autoclave was heated to 60° C., and mixed 30 minutes. The autoclave was then heated to 125° C. and we added PO at 800–850 g/hr<90 PSIG. When all the PO was in, we reacted to constant pressure, for one hour minimum, and three hours maximum. The autoclave was cooled to 70° C. and the contents discharged to nitrogen gas flushed bottles. The hydroxyl number was 278 mg KOH/g.

| Nonionic Surfactant A Intermediate | |
| --- | --- |
| P-402T | 250.0 g |
| 45% KOH | 4.8 g |
| Propylene Oxide | 2318.0 g |

To a prepared one gallon autoclave, we charged P-402T and KOH. The autoclave was sealed, purged and the pressure was checked. The autoclave was heated to 115° C. and evacuated to <10 mmHg. It was then stripped for 30 minutes. The expected 3.5 g volatiles was noted. We relieved the vacuum with nitrogen gas to 2-5 PSIG>

We added PO at 300–325 g/hr<90 PSIG. (If high pressure, react to constant pressure. The autoclave should be vented only if needed. Volatiles should be recorded if venting occurs). When all the PO was in, it was reacted to constant pressure, for four hours minimum, 6 hours maximum. The autoclave was cooled to 80° C. The hydroxyl number was 34.0 mg KOH/g.

| Nonionic Surfactant A + 20 PO | |
| --- | --- |
| Surfactant A Intermediate | 1485 g |
| Propylene Oxide (Mixed) | 243 g |
| Ethylene Oxide (Mixed) | 972 g |

A prepared one gallon autoclave was charged with the base intermediate. The autoclave was sealed, purged and the pressure was checked. It was heated to 110° while evacuating to <10 mmHg, and it was stripped 1 hour. We relieved the vacuum to 2-5 PSIG, and heated to 125° C. We adjusted the pressure to 34 PSIG and added mixed-oxides at 250–275 g/hr<90 PSIG. (If the pressure becomes high, react to constant pressure. Vent only if needed. Record volatiles.) When all reactants were in, we reacted to constant pressure, for one hour minimum, three hours maximum. The hydroxyl number was 19.2 mg KOH/g.

By using the above described liquefied polyoxyalkylene polyols as dispersants, it is possible to produce aqueous flowable concentrates of powdered pesticides which do not require expensive agitation equipment to bring them into solution and which offer ease of handling which represents a real savings to the ultimate user in terms of time and money which is invested in equipment.

The performance of a dispersant in a suspension concentrate, also known as an aqueous flowable, is evaluated by measuring several properties of the suspension, both as is and on dilution to use conditions. The various properties evaluated are listed in the examples which follow. Pour Point: is a measure of the temperature at which a liquid dispersing agent begins to flow. About 40 ml of the liquid dispersing agent, which may be above room temperature, are placed into a glass tube 11½ × 3½ cm. A thermometer is placed in the dispersing agent and the tube and its contents are cooled. The tube is occasionally tilted to determine if the liquid is fluid. The temperature at which the fluid ceases to flow is the pour point.

Evaluation of "as is" Suspension Concentrates

Viscosity: The viscosity of the suspension concentrates was measured at room temperature (25° C.) using a Brookfield LV viscometer.

Pour Out Residue: Long term stability of these suspensions was measured by the amount of sedimentation in the suspension after thirty days storage at room temperature. The percentage of the suspension that will not pour out of the container within one minute was reported as the pour out residue.

Evaluation of Diluted Suspensions

The suspensions were diluted to tank mix concentrations. In the examples, water of 34, 342, and 1000 ppm hardness was used to make the various dilutions and to carry out the several evaluations.

Spontaneity: This is a measure of the suspension's ability to bloom when added to water without agitation. Spontaneity is a qualitative measure of performance. Good bloom refers to the concentrate rapidly forming a cloudy dispersion when poured into water.

Separation: refers to the various phases formed when the pesticide is allowed to stand for a definite period of time. Syneresis is the clear liquid (i.e., no dispersion) that separates above the dispersion. The dispersion consists of the active particles suspended in the aqueous continuous phase. Sedimentation is the active that settles to the bottom. Separation is measured by placing the pesticide formulation in a 100 ml graduated cylinder. The cylinder and its contents are held at room temperature. The volumes of syneresis, dispersion, and sedimentation are measured as percentages of the total formulation.

Reconstitution: refers to the number of times the 100 ml graduated cylinder containing room temperature pesticide formulation has to be inverted to completely redisperse the formulation. The less the number of inversions, the better the dispersing agent.

Percent Suspensibility: a completely dispersed suspension in a 100 ml graduate cylinder is allowed to stand two hours. The top 90 ml of the dispersion are siphoned off and the amount of solids dispersed therein is reported as the % suspensibility.

Zeta Potential: refers to the electrokinetic potential, or potential of a charged particle as calculated from electrokinetic phenomena. It is defined as the potential of the surface at the plane of shear between the particle and the surrounding solution as the particle and the solution move with respect to each other. The absolute zeta potential of a surface increases when a charged surfactant is absorbed on the surface. Nonionic surfactants lower zeta potential by diluting the charge density at the surface.

Ten Inversion Foam Height: The diluted suspension was inverted ten times and the amount of foam that was generated is reported in millimeters.

The modified polyols were evaluated in ATRAZINE ® pesticide formulations. The five dispersants evaluated were Surfactant A and Surfactant B, both of which are commercially used to disperse pesticides, and the three PO modified products based on Surfactant A. The modified polyols were prepared by replacing 7. 10 and 20% of the EO in the hydrophile with propylene oxide by simultaneously feeding the EO/PO mixture into the reactor. The following general formula was used throughout the examples.

| Formulation | |
|---|---|
| Materials | Wt. % |
| ATRAZINE ® pesticide | 45 |
| Ethylene Glycol | 6 |
| FG-10 Antifoam | 0.5 |
| PROXEL GXL biocide | 0.1 |
| Dispersant | 5 |
| Water | qs |

EXAMPLE 1

Pour Points

In general the addition of PO to the EO block helps to lower the point of the dispersing agent as was demonstrated by Patton et al. The Surfactant A +7 PO had the same pour point as Surfactant A, but the molecular weight was a little high. If the molecular weight were lowered, the pour point would also be reduced.

TABLE 1

Pour Points of Dispersing Agents

| Product | Pour Point | Calculated Molec. Wt. |
|---|---|---|
| Surfactant A | 32° C. | 4,931 |
| Surfactant A + 7 PO | 32 | 5,575 |
| Surfactant A + 10 PO | 24 | 5,286 |
| Surfactant A + 20 PO | 9 | 4,775 |
| Surfactant B | 35 | 5,156 |

The addition of the more hydrophobic PO, might be expected to have an adverse affect on the dispersing ability of these surfactants, especially the Surfactant A +20 PO. The following examples show this is not the case.

EXAMPLE 2

Brookfield Viscosity

The viscosities of ATRAZINE ® pesticides suspension concentrates prepared with the PO modified products are comparable to those made with Surfactant A and Surfactant B. Thus liquification of the Surfactant A using PO heteric hydrophobes did not adversely affect the viscosity of the concentrates.

TABLE II

Brookfield LV Viscosity of the Atrazine Suspension Concentrates (CPS, Spindle #2)

| Speed rmp | Surfactant A | Surfactant A + 7 PO | Surfactant A + 10 PO | Surfactant A + 20 PO | Surfactant B |
|---|---|---|---|---|---|
| 6 | 350 | 350 | 325 | 375 | 360 |
| 12 | 220 | 213 | 205 | 225 | 235 |
| 30 | 122 | 125 | 115 | 125 | 120 |
| 60 | 85 | 88 | 83 | 90 | 68 |

EXAMPLE 3

Pour Out Residue

On storage, these suspension concentrates, as do all good suspensions, began to settle. After one month storage, the suspensions were poured out. The amount of residue left in the container after pouring was reported as percent pour out residue. This is a measure of shelf stability. The PO in the modified polyols had little effect on the pour out residue.

TABLE III

One Month Pour Out (% Residue)

| Surfactant A | Surfactant A + 7 PO | Surfactant A + 10 PO | Surfactant B |
|---|---|---|---|
| 2.8 | 3.6 | 3.3 | 2.9 |

EXAMPLE 4

Spontaneity

The spontaneity of the suspensions was also compared. The following table lists the results. The PO modification had spontaneity comparable to the Surfactant A and Surfactant B controls.

TABLE IV

| | Spontaneity | | | | |
|---|---|---|---|---|---|
| Water Hardness | Surfactant A | Surfactant A + 7 PO | Surfactant A + 10 PO | Surfactant A + 20 PO | Surfactant B |
| 34 | E | E | E | E | E |
| 342 | E | E | E | E | E |

TABLE IV-continued

| | Spontaneity | | | | |
|---|---|---|---|---|---|
| Water Hardness | Surfactant A | Surfactant A + 7 PO | Surfactant A + 10 PO | Surfactant A + 20 PO | Surfactant B |
| 1000 | E | E | E | E | E |

E = Excellent, VG = Very Good, G = Good, P = Poor

EXAMPLE 5

Separation

We measured how much the diluted suspensions separated on standing at room temperature. The amounts of syneresis, dispersion, and settling after standing thirty minutes, one hour, and two hours are tabulated below. The inclusion of the PO in the EO blocks did not affect the stability of the diluted dispersion. Thus the liquid products performed as well as the solid Surfactant A and Surfactant B.

TABLE V

SEPARATION OF FORMULATIONS
(% syneresis/% dispersion/% sedimentation by volume)

| Run No. | Time | Water Hardness | Surfactant A | Surfactant A + 7 PO | Surfactant A + 10 PO | Surfactant A + 20 PO | Surfactant B |
|---|---|---|---|---|---|---|---|
| 1 | 30 Min. | 34 | 0/100/0 | 0/100/0 | 0/100/0 | 0/100/0 | 0/100/0 |
| 2 | | 342 | 0/100/0 | 0/100/0 | 0/100/0 | 0/100/0 | 0/100/0 |
| 3 | | 1000 | 0/100/0 | 0/100/0 | 0/100/0 | 0/100/0 | 0/99/1 |
| 4 | 1 Hour | 34 | 0/98/2 | 0/100/0 | 0/100/0 | 0/100/0 | 0/100/0 |
| 5 | | 342 | 0/100/0 | 0/100/0 | 0/100/0 | 0/100/0 | 0/100/0 |
| 6 | | 1000 | 0/99/1 | 0/99/1 | 0/99/1 | 0/99/1 | 0/99/1 |
| 7 | 2 Hour | 34 | 0/100/0 | 0/100/0 | 0/100/0 | 0/100/0 | 0/100/0 |
| 8 | | 342 | 0/100/0 | 0/100/0 | 0/100/0 | 0/100/0 | 0/100/0 |
| 9 | | 1000 | 0/99/1 | 0/99/1 | 0/99/1 | 0/99/1 | 0/99/1 |

EXAMPLE 6

Reconstitution

Once a dispersion had stood for two hours, the amount of agitation needed to re-suspend, or reconstitute, the separated dispersion was recorded. The next table gives the number of times the cylinder had to be inverted in order to reconstitute the dispersion. If one looks at the total inversions for each dispersing agent, there was a slight decrease in the amount of agitation required for reconstitution with the PO modified polyols compared to Surfactant A, and a significant decrease compared to Surfactant B.

TABLE VI

Reconstitution (number of inversions)

| Run No. | Water Hardness | Surfactant A | Surfactant A + 7 PO | Surfactant A + 10 PO | Surfactant A + 20 PO | Surfactant B |
|---|---|---|---|---|---|---|
| 1 | 34 | 8 | 9 | 10 | 10 | 12 |
| 2 | 342 | 12 | 11 | 8 | 12 | 15 |
| 3 | 1000 | 15 | 12 | 12 | 12 | 20 |
| Total | — | 35 | 32 | 30 | 34 | 47 |

EXAMPLE 7

Percent Suspensibility

After the diluted suspension stands for two hours, the percentage of the solids that remain suspended in the top 90% of the sample was reported as percent suspensibility. The following table lists the results of this test. The inclusion of 20 PO in the EO block appeared to increase the percent of solids that remain suspended after two hours, when compared to Surfactant A and Surfactant B. The addition of 7 and 10 PO to the EO blocks had only a slight effect on the amount of solids that remained suspended; however, they would still be considered good dispersants.

TABLE VII

| Run No. | Water Hardness | Percent Suspensibility | | | | |
|---|---|---|---|---|---|---|
| | | Surfactant A | Surfactant A + 7 PO | Surfactant A + 10 PO | Surfactant A + 20 PO | Surfactant B |
| 1 | 34 | 91.7 | 91.7 | 90.6 | 94.6 | 92.3 |
| 2 | 342 | 90.0 | 88.2 | 88.4 | 92.3 | 90.4 |
| 3 | 1000 | 89.0 | 86.2 | 85.0 | 90.0 | 88.2 |

EXAMPLE 8

Zeta Potential

The zeta potentials of the suspensions made using the modified and unmodified polyols were measured. The zeta potentials were in the range expected for good steric dispersants.

TABLE VIII

| Run No. | Water Hardness | Zeta Potential (millivolts) | | | | |
|---|---|---|---|---|---|---|
| | | Surfactant A | Surfactant A + 7 PO | Surfactant A + 10 PO | Surfactant A + 20 PO | Surfactant B |
| 1 | 34 | −3.9 | −11.6 | −9.3 | −12.5 | −8.3 |
| 2 | 342 | −2.1 | −9.8 | −4.9 | −2.6 | −5.0 |
| 3 | 1000 | −1.4 | −6.3 | −7.0 | −4.0 | −3.5 |

EXAMPLE 9

Ten Inversion Foam Height

The addition of 7-PO's in the surfactant produces a dispersion whose foam generation was comparable to the control. The addition of 10 PO's gave surprisingly worse foam than the control, but the addition of 20 PO's gave much lower foam then the controls. It is the desire of each user of such materials to minimize foam.

TABLE IX

| Water Hardness | Surfactant A | Ten Inversion Foam Height (millimeters) | | | |
|---|---|---|---|---|---|
| | | Surfactant A + 7 PO | Surfactant A + 10 PO | Surfactant A + 20 PO | Surfactant B |
| 34 | 12 | 12 | 15 | 8 | 12 |
| 342 | 11 | 10 | 16 | 11 | 10 |
| 1000 | 12 | 14 | 18 | 9 | 16 |
| Total | 35 | 36 | 49 | 28 | 38 |

CONCLUSIONS

The amount of PO added to the EO block represented by these two modified polyols did not negatively affect the excellent dispersing properties of the original surfactants, and in some cases slightly improved them.

Adding PO to the EO block of Surfactant A polyol reduced the pour point of the modified product when compared to Surfactant A and Surfactant B polyols. The modification led to slight changes in the viscosity and pour out residue concentrates of the suspension. Less agitation was required for reconstitution. With PO in the EO blocks, the solids were well suspended. All of these differences indicated that the PO modified polyols were comparable, or slightly better, dispersants, under these test conditions. The zeta potential of the suspensions made with PO modified polyols are in the range for a good steric dispersion. Lastly, including 20% PO in the EO blocks reduced the amount of foam these suspensions generated. Spontaniety and separation of the dispersions made using the lower melting products excellent.

We claim:

1. A stable, aqueous pesticide dispersion composition comprising:
   (a) a water insoluble pesticide;
   (b) A polyoxyalkylene copolymer having surface active properties, said copolymer having the formula

   $$Y[EO,PO)_m(PO)_m(EO,PO)_{m'}H]_m$$

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EP,PO) represents a hydrophilic heteric block having an oxygen/carbon ratio of more than 0.40, m, m' and n are numbers such that the total molecular weight of said hydrophilic heteric block is from about 660 to 4,400, the total molecular weight of said PO hydrophobe is from about 1600 to 3600 and the total molecular weight of said copolymer ranges from about 2200 to 800, said copolymer being about 30 to 55 weight percent hydrophilic with said hydrophilic heteric block comprising from about 5 to 40 weight percent of PO; and
   (c) water, wherein said composition has at least one improved property elected from the group consisting of viscosity, pour out residue, spontaneity, separation, reconstitution, percent suspensibility, zeta potential, and ten inversion foam height, as compared with said composition not having copolymer (b).

2. The aqueous pesticide dispersion composition as claimed in claim 1, wherein said water insoluble pesticide is selected from the group consisting of 2,2-bis(p-methoxyphenyl)-1,1,1-trichloroethane, 2-chloro-2',6'-diethyl-N-(methoxymethyl) acetanilide; a,a,a-trifluoro-2,6-dinitro-N,N-dipropyl-p-toluidine; N-(1-ethylpropyl)-3,4-dimethyl-2,6-dinitrobenzenamine; 2-chloro-4-ethylamino-6-isopropylamino-1,3,5-trazine; 3-(3,4-dichlorophenyl)-1-methoxy-1-methylurea; 3-(3,4-dichlorophenyl)-1,1-dimethylurea; 1-naphthyl-N-methylcarbamate, and mixtures thereof.

3. The aqueous pesticide dispersion composition as claimed in claim 1, wherein said heteric hydrophilic block comprises from about 7 to 40 weight percent of PO.

4. The aqueous pesticide dispersion composition as claimed in claim 1, wherein said water insoluble pesticide is present in said composition in an amount of about 45% by weight.

5. The aqueous pesticide dispersion composition as claimed in claim 4, wherein said copolymer is present in said composition in an amount of about 5% by weight.

6. The aqueous pesticide dispersion composition as claimed in claim 2, further comprising one or more preservatives.

* * * * *

UNITED STATES PATENT AND TRADEMARK OFFICE
CERTIFICATE OF CORRECTION

PATENT NO.   : 5,187,191
DATED        : February 16, 1993
INVENTOR(S)  : Otten et al.

It is certified that error appears in the above-indentified patent and that said Letters Patent is hereby corrected as shown below:

In Claim 1, col. 16, line 43 - add 800-0, thus line 43 should read:

2200-8000.

Signed and Sealed this

Nineteenth Day of December, 1995

Attest:

BRUCE LEHMAN

Attesting Officer        Commissioner of Patents and Trademarks